United States Patent
Windsheimer

(10) Patent No.: US 8,501,110 B2
(45) Date of Patent: Aug. 6, 2013

(54) STERILIZING TUNNEL FOR PHARMACEUTICAL CONTAINERS

(75) Inventor: Manfred Windsheimer, Satteldorf (DE)

(73) Assignee: Robert Bosch GmbH, Stuttgart (DE)

( * ) Notice: Subject to any disclaimer, the term of this patent is extended or adjusted under 35 U.S.C. 154(b) by 1100 days.

(21) Appl. No.: 12/007,499

(22) Filed: Jan. 11, 2008

(65) Prior Publication Data

US 2008/0181826 A1 Jul. 31, 2008

Related U.S. Application Data

(62) Division of application No. 10/470,343, filed as application No. PCT/DE02/02793 on Jul. 30, 2002, now abandoned.

(30) Foreign Application Priority Data

Nov. 29, 2001 (DE) .............................. 101 58 571 U

(51) Int. Cl.
- *A61L 2/04* (2006.01)
- *C11B 1/04* (2006.01)
- *A61L 2/00* (2006.01)

(52) U.S. Cl.
USPC .............................. 422/307; 422/308; 422/22

(58) Field of Classification Search
USPC ............................................ 422/307, 308, 22
See application file for complete search history.

(56) References Cited

U.S. PATENT DOCUMENTS

| | | | |
|---|---|---|---|
| 5,064,614 A * | 11/1991 | Reiss et al. | 422/22 |
| 6,142,065 A * | 11/2000 | Panella et al. | 99/468 |
| 6,297,479 B1 * | 10/2001 | Wefers | 219/388 |
| 6,413,481 B1 * | 7/2002 | Pennekamp et al. | 422/302 |

FOREIGN PATENT DOCUMENTS

| | | |
|---|---|---|
| DE | 1 248 234 | 8/1967 |
| DE | 33 21 195 A1 * | 12/1984 |
| DE | 35 06 788 A1 | 7/1985 |
| DE | 35 10 286 A1 | 9/1986 |
| DE | 37 34 830 A1 | 4/1989 |
| DE | 41 31 258 A1 | 5/1992 |
| DE | 198 46 277 A1 | 4/2000 |
| EP | 1 450 867 B1 | 2/2008 |
| JP | 1-190361 A | 7/1989 |
| JP | 5-7385 U | 2/1993 |
| JP | 2000-109030 A | 4/2000 |

* cited by examiner

*Primary Examiner* — Regina M Yoo

(74) *Attorney, Agent, or Firm* — Michael Best & Friedrich LLP

(57) ABSTRACT

A sterilizing tunnel for pharmaceutical containers has an entry zone, a heating zone, and two cooling zones. The individual zones contain ventilating fan units that generate air currents, which serve to heat and cool the containers that a transport apparatus conveys through the sterilizing tunnel. The heating and cooling units, which operate using the principle of heated and cooled air flow, is supplemented with radiant heat-generating unit. The sterilizing tunnel makes it possible to achieve a uniform heating and cooling of the containers, preventing stress cracks in the containers and permitting intentional heating that makes it possible, for example, for the containers to be coated with a substance.

15 Claims, 3 Drawing Sheets

STERILIZING TUNNEL FOR PHARMACEUTICAL CONTAINERS

CROSS-REFERENCE TO RELATED APPLICATIONS

This application is a Divisional of Ser. No. 10/470,343 filed on Jan. 12, 2004 now abandoned, which is based on a 35 USC 371 application of PCT/DE 02/02793 filed on Jul. 30, 2002.

BACKGROUND OF THE INVENTION

1. Field of the Invention

The invention relates to an improved sterilizing tunnel for pharmaceutical containers.

2. Description of the Prior Art

One sterilizing tunnel of the type with which this invention is concerned is known from DE 198 46 277 C2. Sterilizing tunnels of this kind, which are used in the pharmaceutical industry, particularly for sterilizing ampules, vials, or the like, have ventilating fans in the individual zones along which the containers are conveyed, which produce an air flow that circulates around the containers in a laminar fashion from top toward the bottom. Depending on the zone, the circulated air is scrubbed by means of clean air filters (so-called HEPA filters) disposed above the containers and is heated and cooled by means of heating and cooling units. Due to the flow direction of the air, the heating and cooling of the containers occurs from the direction of the container mouth toward the container bottom, i.e. unevenly over the height of the container, which can damage the containers or produce stress cracks in them, particularly in relatively thin containers or when a container has walls of different thicknesses.

It is also known to coat the containers with emulsion-like substances (e.g. silicone) before entry into the sterilizing tunnel. In this case, the sterilizing tunnel is also used for fixing and baking the substance into the surface of the containers. In the sterilizing tunnels of the prior art in which hot air is circulated through filters, the filters can become clogged with baking residues of the substances, consequently reducing the service life of these filters.

There are also known sterilizing tunnels whose heating units are operated solely by means of radiant heat generators (e.g. infrared radiators).

SUMMARY AND ADVANTAGES OF THE INVENTION

The sterilizing tunnel for pharmaceutical containers according to the invention, has the advantage over the prior art that the containers are thermally treated in a particularly gentle way so that the probability of stress cracks is reduced. This is achieved according to the invention through the additional use of radiant heat-generating heating units that act on the container bottoms so that in concert with the hot air from the ventilating fan units, it is possible to produce a uniform heating of the containers over their entire height.

In order to improve the action of the radiant heat on the container bottoms, it is advantageous for the transport apparatus on which the containers are conveyed to be embodied in the form of a radiation-permeable wire mesh belt.

If the sterilizing tunnel is also intended to be used for coating and baking-on emulsion-like substances, then the invention provides for the use of heating units that generate additional radiant heat in the heating zone, which units are disposed above and/or to the side of the containers. As a result, the coating and baking-on process is at least for the most part already finished by the next time hot air is circulated around the containers, thus reducing the percentage of baking residues in the air that is circulated through the filters.

In order to reduce the susceptibility of the containers to stress cracks, it is likewise advantageous to also provide radiant heat-generating heating units in the cooling zone, at least above the container mouths.

BRIEF DESCRIPTION OF THE DRAWINGS

Two exemplary embodiments of the invention are described in detail herein below, in conjunction with the drawings, in which.

DESCRIPTION OF THE PREFERRED EMBODIMENTS

Figure 1:
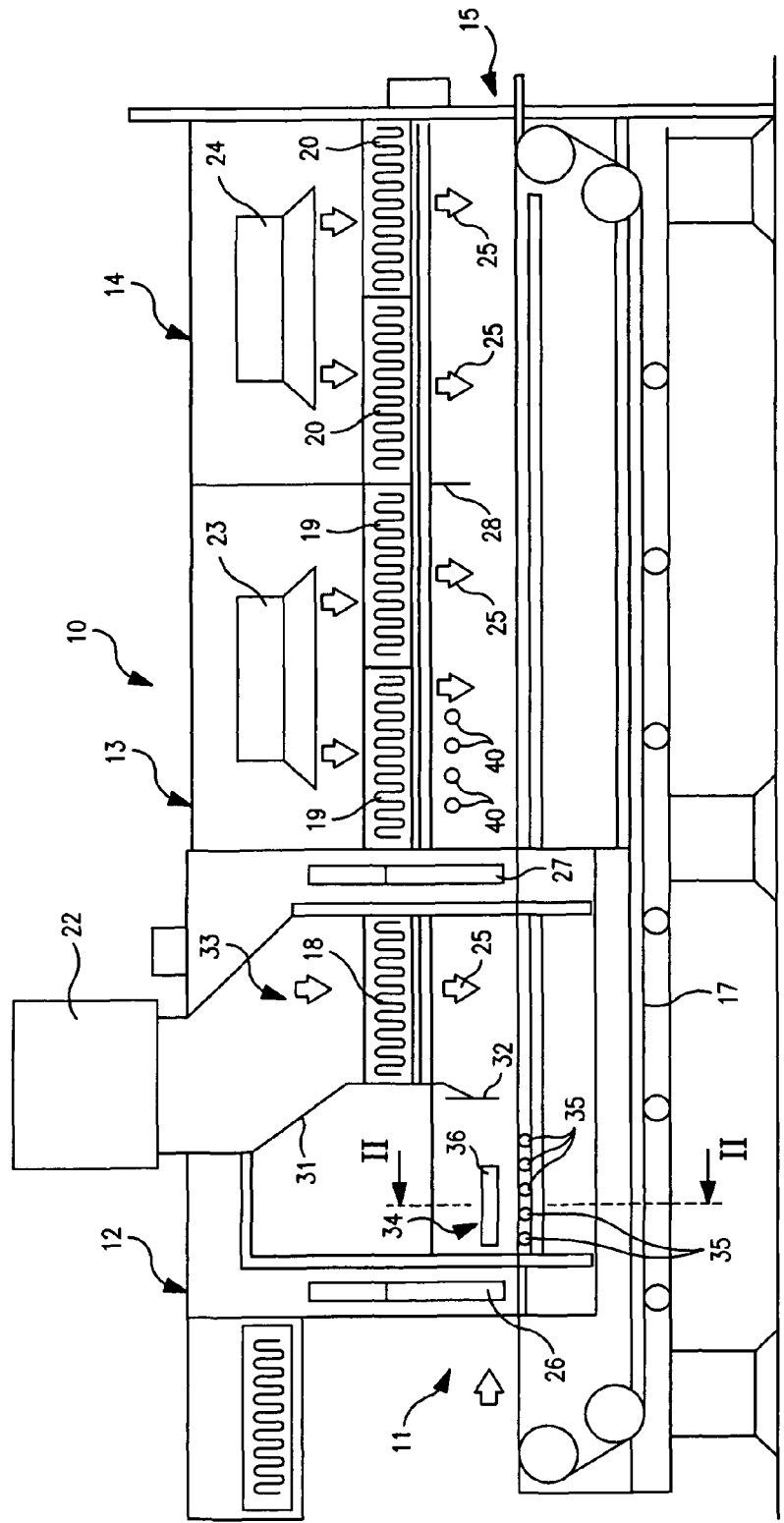
FIG. 1 shows a simplified longitudinal section through a first sterilizing tunnel according to the invention.
Figure 2:
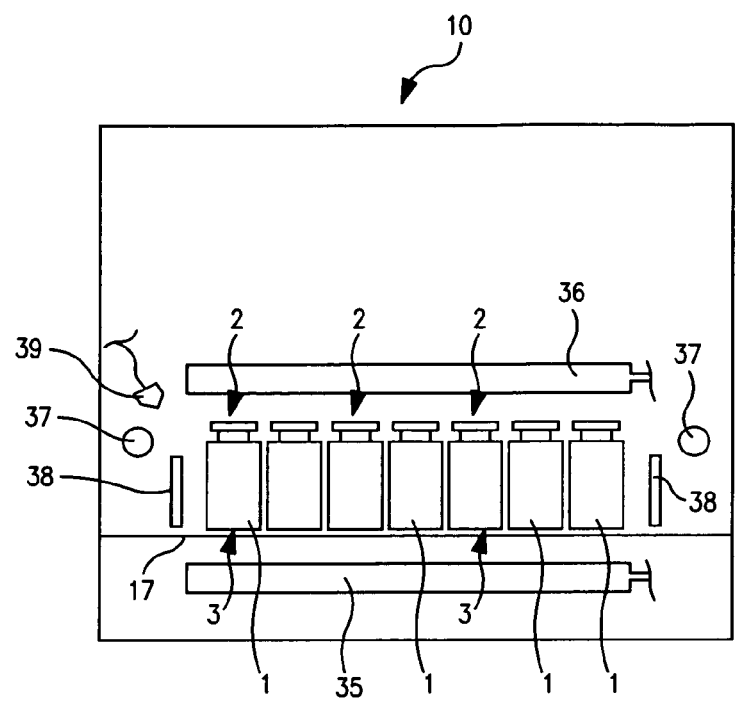
FIG. 2 shows a partial section in the plane II-II of FIG. 1 during operation of the first sterilizing tunnel.

The first sterilizing tunnel 10 according to the invention schematically depicted in FIG. 1 is essentially comprised of an entry zone 11, a heating zone 12, and two cooling zones 13, 14. Pharmaceutical containers 1 such as ampules, vials, or the like, which come from a cleaning machine, not shown, are supplied into the sterilizing tunnel 10 from the entry zone 11 and leave the tunnel at its opposite end 15 after the cooling zone 14, in order to then be further processed in the subsequent filling and closing machines, which are not shown.

A horizontal, preferably continuously driven, endless conveyor belt 17 serves to transport the containers 1 through the individual zones inside the sterilizing tunnel 10. Preferably, the conveyor belt 17 is embodied as an air-permeable wire mesh belt made of stainless steel.

Large-area filter elements 18, 19, and 20 are disposed above the conveyor belt 17 in the different zones of the sterilizing tunnel 10. The filter elements 18, 19, and 20 cooperate with ventilating fan units 22, 23, and 24, which are each associated with a respective zone and each serve to circulate the air in a respectively closed circuit. The air flows generated by the ventilating fan units 22, 23, and 24, which circulate in the form of so-called laminar flow currents (flow arrows 25) around the containers 1 essentially from top to bottom during their transport through the sterilizing tunnel 10, are temperature-controlled by means of heating and cooling units that are not shown. To that end, temperature sensors are placed in the individual zones, which supply the measured temperatures as input values to the control unit of the sterilizing tunnel 10. The control unit then appropriately regulates the heating and cooling units, and is assisted by inlet and outlet air flaps, not shown, that are also disposed in the zones, which additionally serve to compensate for leakage and overflow losses. Furthermore, vertically adjustable sluices 26, 27, and 28, whose position is adapted to the respective container height, are positioned both between zones and within zones in order to reduce the above-mentioned overflow losses between the individual zones.

The air flows generated by the ventilating fan units 22, 23, and 24, which circulate around the containers 1 from above, i.e. from the container mouth 2 toward the container bottom 3, result in an uneven temperature distribution over the height of the containers. As a result, the container mouths 2 have a higher temperature than the container bottoms 3 as they pass through the heating zone 12. This is because the hot air in the heating zone 12 comes into contact with the container mouth 2 first.

The sterilizing tunnel 10 is particularly designed to permit deliberate influence to be exerted on the temperature distribution along the height of the containers 1 in order to thus prevent thermal stresses that can damage the containers 1 and is also designed to permit favorable influence to be exerted on the baking of emulsion-like particles into the inner walls of the containers. In order to accomplish this, the heating zone 12 is divided into two regions 33 and 34 by means of a dividing wall 31, whose end oriented toward the conveyor belt 17 is embodied as a vertically adjustable intermediary way 32. In the one region 33, the ventilating fan unit 22 provides a heated air flow, whereas the other region 34 situated on the side oriented toward the entry zone 11 is provided with a number of radiant heat-generating heating units 35, 36, 37. This region 34 includes a forward section which is where the containers enter the heating zone 12.

The heating units 35, 36, 37, which are in particular embodied in the form of infrared radiators and in the exemplary embodiment are embodied as rod-shaped, are disposed underneath the radiation-permeable conveyor belt 17 close to the container bottoms 3, above the conveyor belt 17 close to the container mouths 2, and if need be, beside the conveyor belt 17 at the same height as the container mouths 2 outside of stationary or mobile lateral guides 38 for the conveyor belt 17; in the exemplary embodiment, the heating units 35, 36 extend lateral to the travel direction of the containers 1 through the sterilizing tunnel 10 and the heating units 37 extend along this travel direction. At least some of the units 35 are positioned in the forward section so as to provide a controlled and precise heating of the bottoms of the containers so that during their heating up phase thermal stress cracks are avoided. Furthermore, in the region 34, there is also at least one temperature sensor 39, which is coupled to the control unit of the sterilizing tunnel 10 so as to help to accurately control the heating of the containers.

Depending on the intended use, the heating units 35, 36, 37 make it possible to provide an intentionally more intense preheating of particular container regions, for example the container bottoms 3, in order to prevent thermal stresses in the containers 1 in the subsequent further heating by means of the air flow in region 33. In this instance, the heating units 35 oriented toward the container bottoms 3 are set to a higher temperature than the other heating units 36, 37.

In addition, if an emulsion-like substance (e.g. silicone), is used to coat the container 1, it should already be baked-on in the region 34 so that possible baking residues place as little subsequent strain as possible on the filter element 18 in the region 33. In this instance, the radiant heat of the heating units 35, 36, 37 can be set very aggressively, so that the temperature inside the containers 1, which is required for coating them, is reached within an extremely short period of time and is then reduced again if need be in the region 33.

Figure 4:
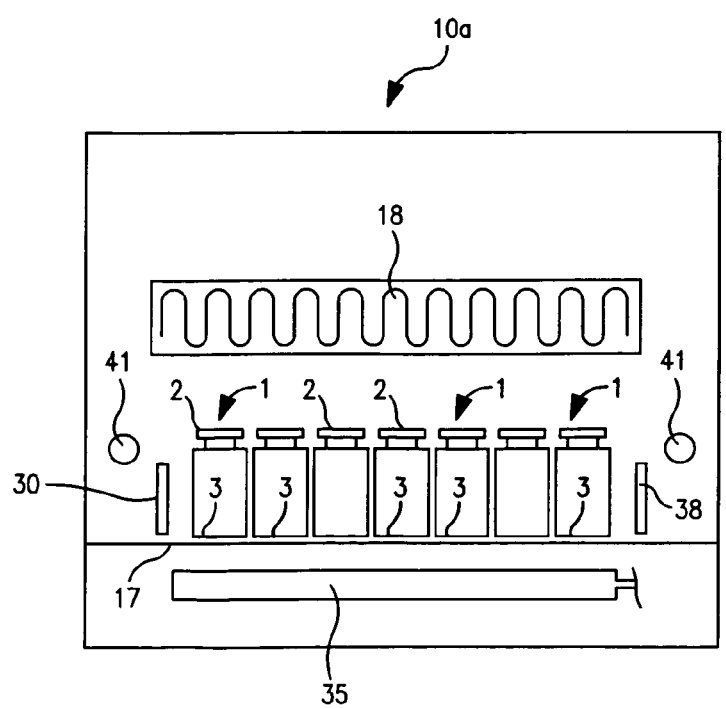
FIG. 4 shows a partial section in the plane IV-IV of FIG. 3 during operation of the second sterilizing tunnel.
Figure 3:
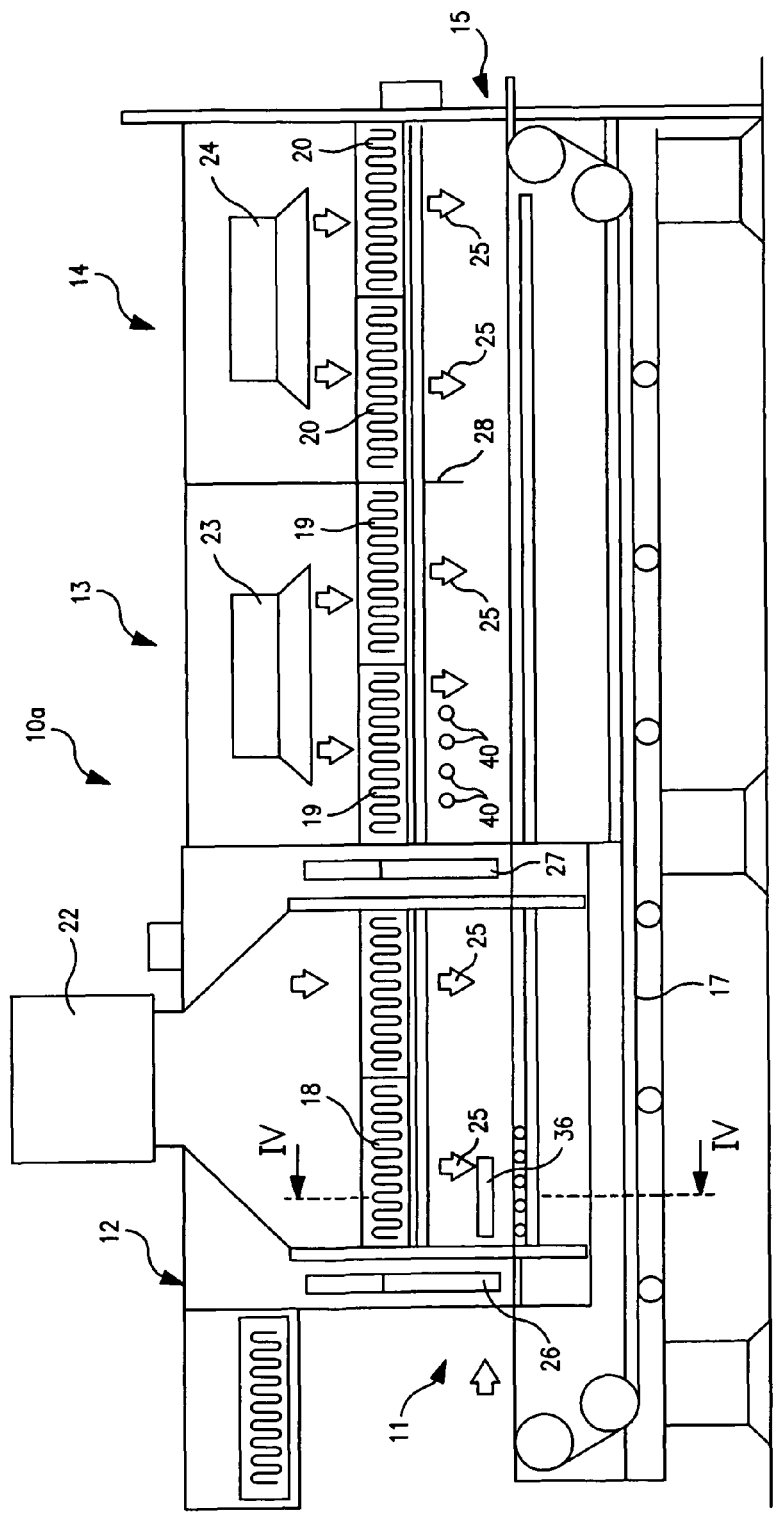
FIG. 3 shows a simplified longitudinal section through a second sterilizing tunnel according to the invention.

By contrast with the sterilizing tunnel 10, in the second sterilizing tunnel 10a shown in FIGS. 3 and 4, the heating zone 12 is only provided with additional heating units 35 underneath the radiation-permeable conveyor belt 17 and with heating units 37 disposed to the side, outside the lateral guides 38 in a manner analogous to the sterilizing tunnel 10, but no radiant heat-generating heating units are provided above the containers 1. Instead, the containers 1 are heated with hot air from above by means of the ventilating fan unit 22 in the entire heating zone 12, from which it also follows that the sterilizing tunnel 10a does not contain a dividing wall 31 of the type provided in the sterilizing tunnel 10 that divides the heating zone 12 into different regions.

In addition, in the sterilizing tunnel 10a, the first cooling zone 13 is provided with additional heating units 40, 41, which also generate radiant heat. These heating units 40, 41, which are also rod-shaped, are provided above the container mouths 2 on the side oriented toward the heating zone 12, as well as laterally, outside the lateral guides 38, at the same height as the container mouths 2, and are controlled by means of a temperature sensor, not shown, which is disposed in the cooling zone 13 close to the heating units 40 and is coupled to the control unit of the sterilizing tunnel 10.

The heating units 40, 41 make it possible for the containers 1, which are transferred out of the heating zone 12 and have a relatively high temperature, to be cooled down somewhat less rapidly in the vicinity of their container mouths 2, thus permitting a more uniform cooling of the containers 1 on the whole. The arrangement of additional heating units 35, 37, 40, 41 embodied in the sterilizing tunnel 10a consequently makes it possible to achieve a heating and cooling of the containers 1 that is gentle to the material in order to avoid thermal stresses and prevent heat cracks in the containers 1.

The two sterilizing tunnels 10, 10a according to the invention can be modified in numerous ways without going beyond essence of the invention, which is comprised of providing additional radiant heat-generating heating units in the sterilizing tunnel 10, which in cooperation with air flows generated by the ventilation fan units, produce a uniform heating and uniform cooling of the containers 1. It is therefore conceivable, for example, to omit the heating units 36, 37 at the top and at the sides. Furthermore, the sterilizing tunnel 10 can also have the heating units 40, 41 disposed in the cooling zone 13 of the sterilizing tunnel 10a, in order to treat the containers 1 in a particularly gentle fashion with regard to thermal stresses.

The foregoing relates to preferred exemplary embodiments of the invention, it being understood that other variants and embodiments thereof are possible within the spirit and scope of the invention, the latter being defined by the appended claims.

The invention claimed is:

1. A sterilizing tunnel for pharmaceutical containers, comprising:
   a heating zone;
   at least one cooling zone;
   a transport apparatus that conveys the containers through the heating zone and the at least one cooling zone where the containers are sterilized;
   laminar flow means within the heating zone for generating air currents that circulate around the containers in the heating zone which heat the containers, and laminar flow means within the at least one cooling zone for generating air currents that circulate around the containers in the at least one cooling zone, the laminar flow means embodied by a ventilating fan unit disposed above the transport apparatus in each zone; and
   at least in the region of the heating zone, in addition to the laminar flow means, at least one radiant heat-generating heating unit acting on the container bottoms, wherein the heating zone is divided into a first region and a second region, and the at least one radiant heat-generating heating unit is disposed in the first region, and wherein the first region is separated by from the second region by means of a dividing wall, and the second region contains the ventilating fan unit which acts on the containers while they are in the heating zone.

2. The sterilizing tunnel according to claim 1, wherein the at least one radiant heat-generating heating unit is disposed in a forward section of the heating zone with respect to a direction of conveying of the containers for heating the containers prior to the laminar flow heating means.

3. The sterilizing tunnel according to claim 2, wherein the transport apparatus comprises a radiation-permeable wire mesh belt, the at least one heating unit being disposed on a side of the transport apparatus opposite from the containers.

4. The sterilizing tunnel according to claim 1, wherein the transport apparatus comprises a radiation-permeable wire mesh belt, the at least one heating unit being disposed on a side of the transport apparatus opposite from the containers.

5. The sterilizing tunnel according to claim 4, wherein the at least one radiant heat-generating heating unit heats the containers to a predetermined temperature at which point an emulsion-like coating on the inner walls of the containers is baked on prior to the containers entering the ventilating fan unit so that any possible baking residues do not interfere with the ventilating fan unit.

6. The sterilizing tunnel according to claim 1, further comprising additional radiant heat-generating heating units disposed in the first region above and to the side of the containers.

7. The sterilizing tunnel according to claim 6, further comprising at least one additional radiant heat-generating heating unit disposed in the region of the cooling zone, which is on the side of the cooling zone which is oriented toward the heating zone.

8. The sterilizing tunnel according to claim 7, wherein the at least one additional heating unit is disposed above the containers.

9. The sterilizing tunnel according to claim 6, wherein the at least one radiant heat-generating heating unit heats the containers to a predetermined temperature at which point an emulsion-like coating on the inner walls of the containers is baked on prior to the containers entering the ventilating fan units so that any possible baking residues do not interfere with the ventilating fan unit.

10. The sterilizing tunnel according to claim 1, further comprising at least one additional radiant heat-generating heating unit disposed in the cooling zone, on the side of the cooling zone which is oriented toward the heating zone.

11. The sterilizing tunnel according to claim 10, wherein the at least one additional heating unit is disposed above the containers.

12. The sterilizing tunnel according to claim 1, further comprising a temperature sensor disposed in the vicinity of the at least one heating unit, the temperature sensor cooperating with a control unit of the sterilizing tunnel.

13. The sterilizing tunnel according to claim 1, wherein the at least one radiant heat-generating heating unit heats the containers to a predetermined temperature at which point an emulsion-like coating on the inner walls of the containers is baked on prior to the containers entering the ventilating fan unit so that any possible baking residues do not interfere with the ventilating fan unit.

14. The sterilizing tunnel according to claim 1, wherein the first region includes additional heating unit which, in cooperation with the at least one radiant heat-generating heating unit, provides more intense preheating to particular regions of the containers.

15. The sterilizing tunnel according to claim 14, wherein one of the particular regions of the containers is their bottoms.

* * * * *